US008864779B2

(12) United States Patent
Kohl et al.

(10) Patent No.: US 8,864,779 B2
(45) Date of Patent: Oct. 21, 2014

(54) DEVICE FOR INTRACORPOREAL APPLICATION OF AUXILIARY MEDICAL MATERIAL

(75) Inventors: Thomas Kohl, Bonn (DE); Martin Blocher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 1189 days.

(21) Appl. No.: 12/171,852

(22) Filed: Jul. 11, 2008

(65) Prior Publication Data

US 2009/0024073 A1 Jan. 22, 2009

(30) Foreign Application Priority Data

Jul. 12, 2007 (DE) .................... 10 2007 032 482

(51) Int. Cl.
*A61B 17/03* (2006.01)
*A61B 17/34* (2006.01)
*A61F 15/00* (2006.01)
*A61F 2/00* (2006.01)
*A61B 17/88* (2006.01)

(52) U.S. Cl.
CPC ........... *A61B 17/3468* (2013.01); *A61F 15/005* (2013.01); *A61F 2/0063* (2013.01); *A61F 2002/0072* (2013.01); *A61B 17/8861* (2013.01)
USPC ........................................................ 606/151

(58) Field of Classification Search
USPC ..................................................... 604/11–15
See application file for complete search history.

(56) References Cited

U.S. PATENT DOCUMENTS

| 5,147,316 | A | * | 9/1992 | Castillenti ................ 604/164.04 |
| 5,263,969 | A |   | 11/1993 | Phillips |
| 5,464,403 | A | * | 11/1995 | Kieturakis et al. ................ 606/1 |
| 5,591,207 | A | * | 1/1997 | Coleman ....................... 606/232 |
| 5,607,477 | A | * | 3/1997 | Schindler et al. .......... 623/23.72 |
| 5,814,058 | A |   | 9/1998 | Carlson et al. |
| 6,419,639 | B2 | * | 7/2002 | Walther et al. ................ 600/562 |
| 8,221,440 | B2 | * | 7/2012 | Kullas et al. .................. 606/151 |
| 8,262,557 | B2 | * | 9/2012 | Chapman et al. ............... 600/37 |
| 8,317,808 | B2 | * | 11/2012 | Levin et al. ................... 606/151 |
| 2005/0192597 | A1 | * | 9/2005 | Boebel et al. ................. 606/148 |
| 2009/0299352 | A1 | * | 12/2009 | Zerfas et al. ................... 606/15 |

FOREIGN PATENT DOCUMENTS

| DE | 69320258 T2 | 4/1999 |
| DE | 69429878 T2 | 8/2002 |
| DE | 69832288 T2 | 7/2006 |
| EP | 0581036 A1 | 2/1994 |
| EP | 0625334 A1 | 11/1994 |
| EP | 1357872 B1 | 11/2003 |
| WO | 2007056297 A2 | 5/2007 |

OTHER PUBLICATIONS

European Search Report; EP 08 01 2342; Dec. 10, 2008; 6 pages.
German Search Report, Jan. 1, 2006, 4 pages.

* cited by examiner

*Primary Examiner* — Susan Su
(74) *Attorney, Agent, or Firm* — St. Onge Steward Johnston & Reens LLC

(57) ABSTRACT

The invention relates to a device for intracorporeal application of auxiliary medical material, in particular for bio-materials and wound applications, having a hollow application tube for inserting the auxiliary medical material into the surgical area. To create a device for intracorporeal application of auxiliary medical material that ensures simple handling and a secure application of the auxiliary medical material in the surgical area, the invention is characterized by a winding insert that can be inserted into the hollow application tube and can be slid in the longitudinal direction of the application tube and on which it is possible to wind the auxiliary medical material that is to be applied.

13 Claims, 4 Drawing Sheets

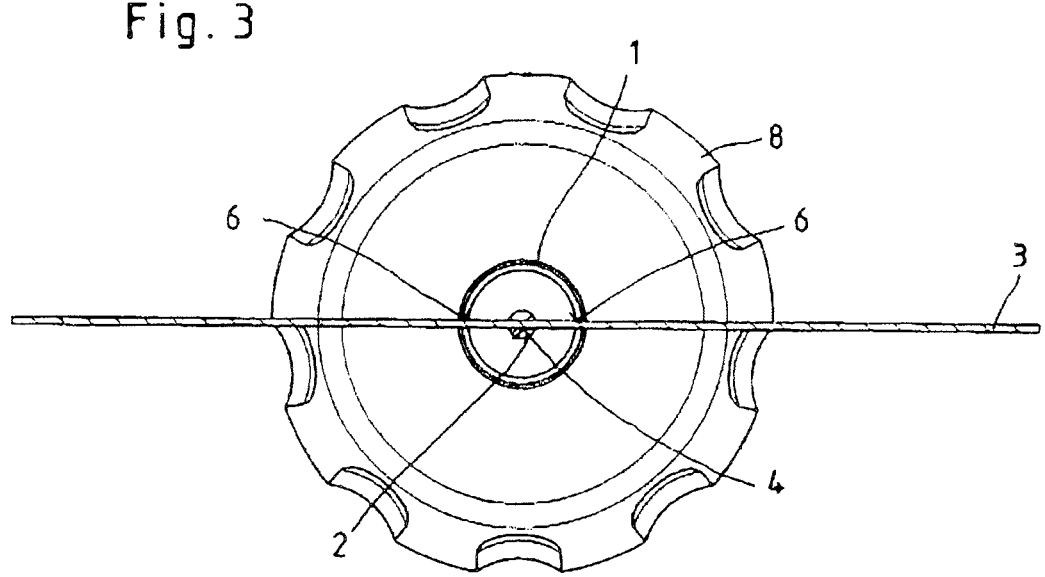
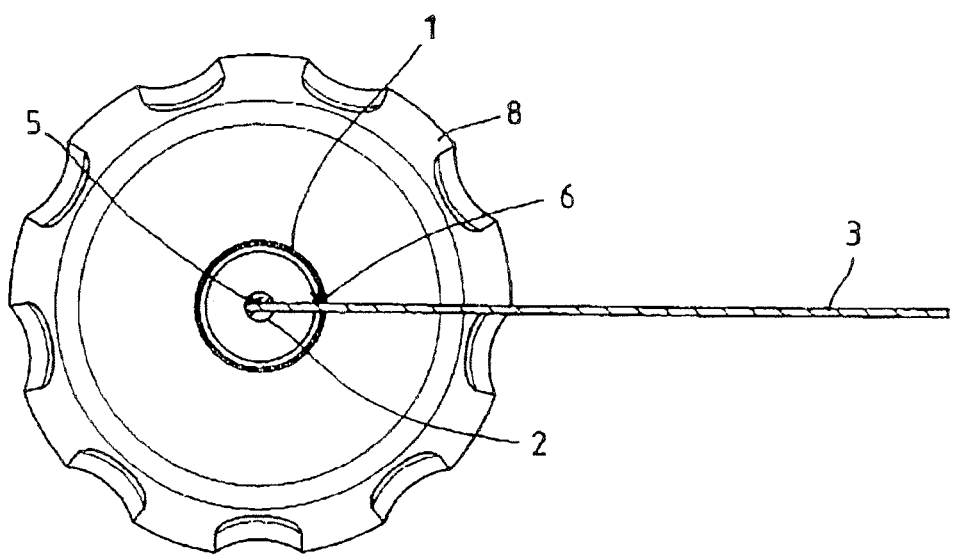

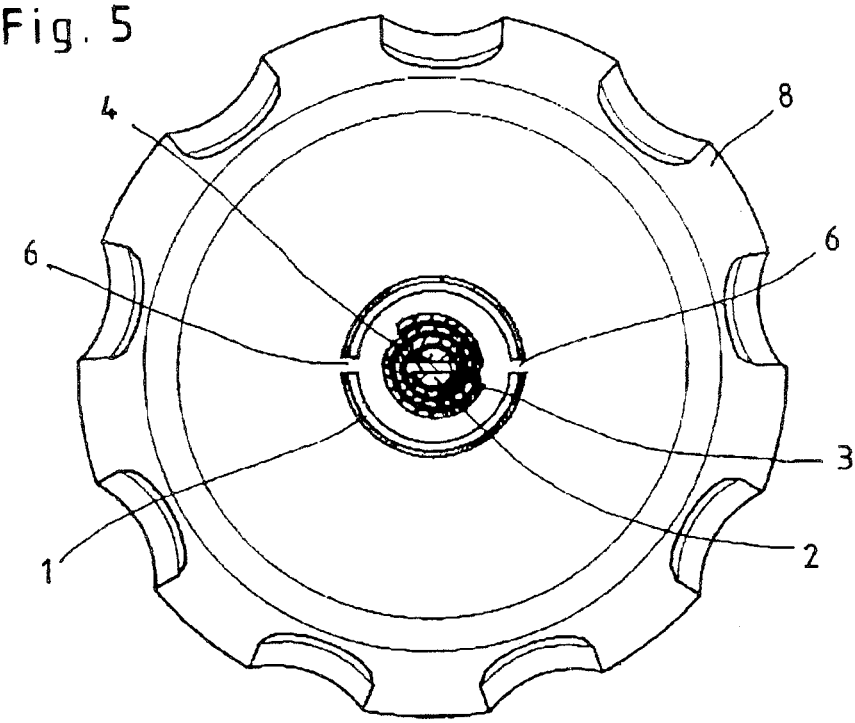
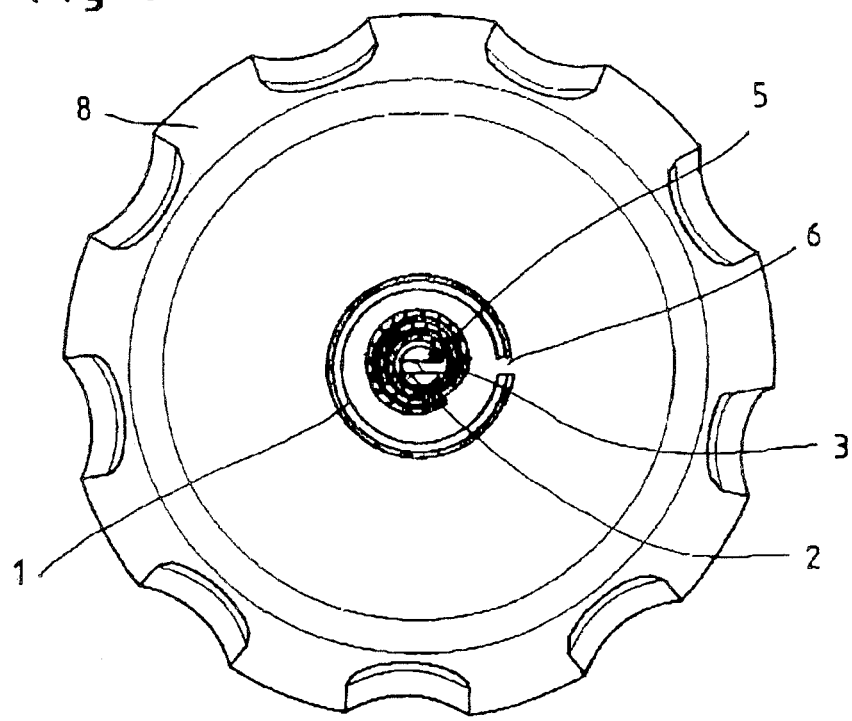

DEVICE FOR INTRACORPOREAL APPLICATION OF AUXILIARY MEDICAL MATERIAL

CROSS-REFERENCE TO RELATED APPLICATIONS

The present application claims priority of German patent application No. 10 2007 032 482.2 filed on Jul. 12, 2007, the content of which is incorporated herein by reference.

FIELD OF THE INVENTION

The invention relates to a device for intracorporeal application of auxiliary medical material, in particular for biomaterials and wound applications, having a hollow application tube for inserting the auxiliary medical material into the surgical area.

BACKGROUND OF THE INVENTION

In various fields of surgery, in particular of endoscopic surgery, it is necessary to introduce auxiliary medical material such as wound applications or bio-material devices into the surgical area and to apply them on the site under tightly compressed conditions.

It is a known practice, for instance, in hernia operations (hernia inguinalis) to use a net-type tissue to join fascia gaps that need to be closed, said tissue being inserted into the surgical area by means of a trocar sleeve. To this end, the tissue net is rolled together or folded manually and inserted into the trocar sleeve and by means of a grasping forceps pushed into the surgical area. The disadvantage with this described procedure, in addition to the great manual complexity of rolling or folding and then inserting the tissue, reduced in size in this manner, into the trocar sleeve, is the risk of damaging the tissue in inserting it into the trocar sleeve.

It is consequently the object of the invention to create a device for intracorporeal application of auxiliary medical material, so that said device is simple to use and also ensures safe application of the auxiliary medical material in the surgical area.

SUMMARY OF THE INVENTION

This object is fulfilled according to invention by means of a winding insert that can be inserted into the hollow application tube and pushed in the longitudinal direction of the application tube, and onto which the auxiliary medical material that is to be applied can be wound up.

Because of the inventive use of the winding insert that can be inserted into the application tube, it is possible for the first time to dispense with manual rolling or folding of the auxiliary medical material that is to be applied. The winding insert along with the auxiliary medical material that is to be wound up onto the winding insert, in addition, can be shoved in the longitudinal direction of the application tube in order to move the auxiliary medical material into the surgical area.

It is proposed, with a practical embodiment of the invention, that the winding insert and the application tube, set inside one another, should be able to rotate with respect to one another around the instrument's longitudinal axis. This reciprocal rotatability of the components alleviates the winding-up and winding-down of the auxiliary medical material onto the winding insert or down from the winding insert.

In order to affix the auxiliary medical material to the winding insert, it is proposed with a first embodiment of the invention that the auxiliary medical material should be attachable onto the winding insert, for instance by configuring a slit in the winding insert for inserting one end of the auxiliary medical material.

According to an alternative embodiment, the auxiliary medical material is affixed onto the winding insert by means of a slit that is configured to pass through the winding insert and into which the auxiliary medical material can be inserted.

According to a practical embodiment of the invention it is proposed that the winding insert should be configured, at least in the area where the auxiliary medical material is to be inserted, as a wire pin that can be inserted into the application tube, and that is preferably of Ni—Ti construction.

To facilitate handling of the inventive device, it is further proposed with the invention that the winding insert should be insertable into the application tube in the axial direction in predetermined catching stages. These catching stages constitute predetermined insertion depths of the winding insert into the application tube, for instance an insertion position and an application position, and thus make possible a safe and uniform operation of the device.

It is further proposed with the invention that at least one opening should be configured in the application tube running in the axial direction for inserting the auxiliary medical material. This window-type opening in the application tube makes it possible to attach the auxiliary medical material onto the winding insert when the winding insert is inserted into the application tube. For this purpose the auxiliary medical material is conducted through the opening into the interior of the application tube and secured, for instance, with one end in the slit of the winding insert. By means of subsequent rotation of the winding insert and/or of the application tube, the auxiliary medical material is drawn into the application tube and wound around the winding insert.

According to a practical embodiment of the invention, two openings are configured in the application tube approximately opposite to one another and running in the axial direction. This embodiment is advantageous, in particular, in the case of large or long auxiliary medical material, because it allows for more rapid unwinding of the auxiliary medical material onto the winding insert. For this purpose, the auxiliary medical material is moved through an opening into the interior of the application tube and inserted through the cut-through slit of the winding insert until the auxiliary medical material emerges again from the application tube through said tube's opposite opening. By subsequent rotation of the winding insert and/or of the application tube, the auxiliary medical material is drawn into the application tube and is wound around the winding insert twofold.

The operation of the application tube and winding insert, especially during contrary rotation of the components, can be facilitated according to the invention in that a handle is positioned on the proximal end of the application tube and/or of the winding insert.

It is finally proposed with the invention that the auxiliary medical material should be an auxiliary medical material for a hernia operation or the like. In a hernia operation the mesh bio-materials or mesh implants consisting of bodily or non-bodily tissue are used to bridge the corresponding fascia gaps.

Further characteristics and advantages of the invention are explained with reference to the appended illustrations, in which two embodiments of an inventive device for intracorporeal application of auxiliary medical material are depicted in merely exemplary terms, with restricting the invention to such embodiments.

BRIEF DESCRIPTION OF THE DRAWINGS

FIG. 3 shows an enlarged cross-section along the reference line III-III of FIG. 1.

FIG. 4 shows a side view corresponding to FIG. 3, but showing a second embodiment of the invention.

FIG. 5 shows a schematic sketch of the winding of the auxiliary medical material onto a winding insert of FIG. 3.

FIG. 6 shows a schematic view of the winding of the auxiliary medical material onto a winding insert as in FIG. 4.

DETAILED DESCRIPTION OF THE INVENTION

Figure 1:
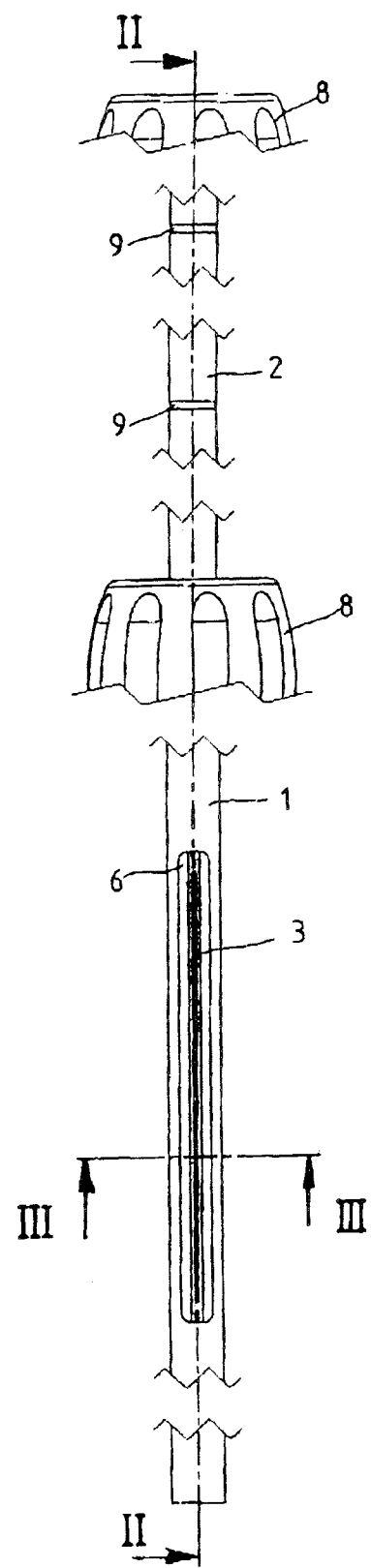
FIG. 1 shows a side view of an inventive device for intracorporeal application of auxiliary medical material.
Figure 2:
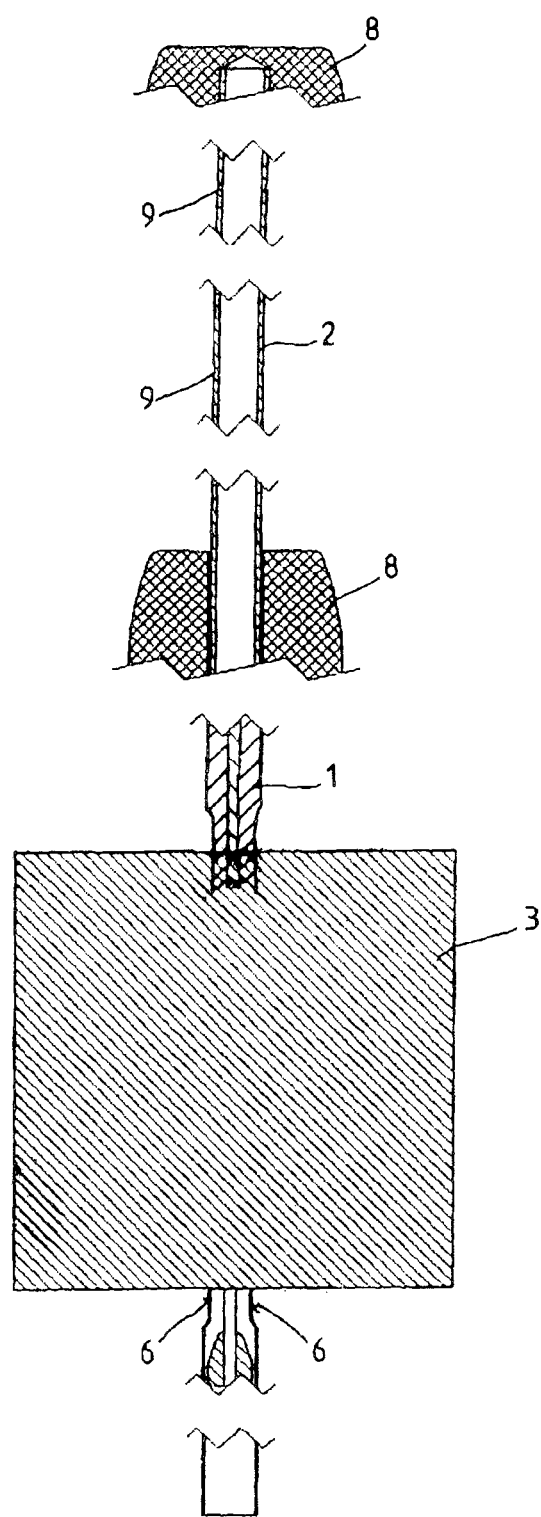
FIG. 2 shows a longitudinal section along the reference line II-II of FIG. 1.

The device depicted in FIGS. 1 and 2 for intracorporeal application of auxiliary medical material consists essentially of a hollow outer application tube 1 and a winding insert 2 that can be inserted into the application tube 1 and can be slid in the longitudinal direction of the application tube 1.

As can be seen in particular from FIGS. 5 and 6, the winding insert 2 serves to hold and insert auxiliary medical material 3, which is inserted into the surgical area by means of the application tube 1. For this purpose the auxiliary medical material 3 is affixed to the winding insert 2 and is wound onto the winding insert 2 before the auxiliary medical material 3, wound onto the winding insert 2, is introduced through the application tube 1 into the surgical area.

The affixing of the auxiliary medical material 3 on the winding insert 2 occurs in the first embodiment, shown in FIG. 3, by means of a traversing slit 4 running through the winding insert 2, through which the auxiliary medical material 3 is pushed until the auxiliary medical material 3 extends outward on both ends, preferably by the same length, from the traversing slit 4. By rotating the winding insert 2, the auxiliary medical material 3 can now be wound onto the winding insert 3 two-fold, as shown schematically in FIG. 5.

According to the second embodiment, shown in FIG. 4, the auxiliary medical material 3 is affixed onto the winding insert 2 in such a way that a one-sided slit 5 is configured in the winding insert 2, into which one end of the auxiliary medical material 3 can be inserted. By rotating the winding insert 2, the auxiliary medical material 3 is now wound onto the winding insert 2, as shown schematically in FIG. 6.

The auxiliary medical material 3 can consist of, for instance, wound dressings or bio-material, which when assembled is inserted into the surgical area and finally spread over the surgical area on the spot and applied to the corresponding application site.

An area of application for this device can be, for instance, hernia operations, in which the auxiliary medical material is made up of mesh bio-material or mesh implants consisting of bodily or non-bodily tissue in order to bridge the corresponding fascia gap.

Theoretically all areas of surgical applications can be considered in which a wound area or incision is to be bridged and/or closed by means of a flat-shaped auxiliary medical material 3, such as in surgery in the abdominal area in cases of stomach or intestinal penetrations or in fetoscopy for closing Spina bifida. It is also possible to use this device for intracorporeal treatment of wounds, for instance fetal head injuries, with bandages and other flat wound applications.

In addition to the possibility of winding the auxiliary medical material 3 onto the winding insert 2 when it is outside the application tube 1, and only then inserting the winding insert 2 wound up with the auxiliary medical material 3 into the application tube 1, there is also the preferred possibility as shown in FIGS. 1 through 6 of affixing the auxiliary medical material 3 to the winding insert 2 and of winding it onto the winding insert 2 only when it has been inserted into the application tube 1.

For this purpose, in the outer lining of the application tube 1 at least one window-type opening 6 is configured which runs in the axial direction of the application tube 1 and through which the auxiliary medical material 3 can be inserted into the application tube 1 to be affixed onto the winding insert 2, as shown in FIG. 1. In the embodiment of the application tube 1 shown in FIG. 1, the window-type opening 6 is configured as a gap 6, although other configurations are also possible which allow the auxiliary medical material 3 to be inserted into the application tube for affixing onto the winding insert 2.

For the embodiment shown in FIGS. 4 and 6, in which the auxiliary medical material 3 is wound once around the winding insert 2, it is sufficient to configure only one gap 6 in the application tube 1. The embodiments shown in FIGS. 4 and 6 are distinguished, however, with respect to the traversing slit 4 and the one-sided slit 5 that are configured in the winding insert 2. While, according to FIG. 1, only the one-sided slit 5 is configured in the winding insert 2, into which one end of the auxiliary medical material 3 can be inserted, in the embodiment seen in FIG. 6 a traversing slit 4 is configured running through the winding insert 2, through which the auxiliary medical material 3 can be passed. This embodiment offers the auxiliary medical material 3 that is affixed onto the winding insert 2 a better grip than the use of the one-sided slit 5 that does not go all the way through.

The embodiment shown in FIGS. 2 and 5 with the traversing slit 4 running through the winding insert 2 and the double-wound auxiliary medical material 3, on the other hand, requires two gaps 6 in the application tube 1 so that the auxiliary medical material 3, after it is secured in the traversing slit 4 of the winding insert 2, can also extend out of the application tube 1 on both ends 1.

To wind the auxiliary medical material 3, which has been affixed in said manner onto the winding insert 2, onto the winding insert 2 proceeds thereafter by rotating the winding insert 2 and/or the application tube 1 around the instrument longitudinal axis 7, although in the event that both components 1 and 2 are rotated, the application tube 1 and winding insert 2 must be rotated in contrary directions. By thus rotating at least one component 1 or 2 with respect to the other component 2 or 1, the auxiliary medical material 3 that is affixed onto the winding insert 2 is drawn into the application tube 1 and wound in layers around the winding insert 2.

To ensure that the winding insert 2 can also be slid axially in the application tube 1 with the auxiliary medical material 3 wound onto it, the winding insert 2 is configured as a wire pin that reduces the diameter of the winding insert 2, at least in the area that receives the auxiliary medical material 3, as can be seen in FIG. 2. Contrary to the illustrated form of the wire pin with circular cross-section, other cross-section shapes can also be employed.

In the other areas the winding insert 2 is advantageously configured in tubular form, so that the outer diameter of the winding insert 2 corresponds essentially to the inner diameter of the application tube 1, to ensure smooth, non-tilting guidance of the winding insert 2 inside the application tube 1.

Operation of the application tube 1 and winding insert 2, in particular the rotation of the components 1 and 2, is facilitated in the illustrated embodiment in that a handle 8 that is as ergonomically designed as possible is configured on the proximal end both of the application tube 1 and of the winding insert 2.

Assembly and operation of the device in the configuration just described for intracorporeal application of auxiliary medical material occur as follows.

In the first working step the winding insert 2 is inserted into the hollow application tube 1 with the distal end in front when viewed from the proximal end until the winding insert 2 assumes the position shown in FIG. 1, in which the slit 4 running through the winding insert 2, or else only the one-sided slit 5, is positioned in the area of the at least one window-type gap 6 of the application tube 1.

For this first working step and also the following steps, in order to maintain constantly the correct insertion depth of the winding insert 2 into the application tube 1, various catch steps 9 are configured on the winding insert 2 in the illustrated embodiment as can be seen from FIG. 1, so that each catch step 9 corresponds to a particular insertion depth of the winding insert 2 into the application tube 1 and marks a corresponding working step.

After inserting the winding insert 2 into the application tube 1 as far as the previously described first notch step, the auxiliary medical material 3 is then affixed onto the winding insert 2, for example by passing it through the completely traversing slit 4, as shown in FIG. 1. Then the winding insert 2 and/or application tube 1 are rotated with respect to one another around the instrument longitudinal axis 7, so that the auxiliary medical material is drawn into the application tube 1 and winds itself onto the winding insert 2.

In the next working step the winding insert 2 equipped with the wound-on auxiliary medical material 3 is inserted further into the application tube 1 in the distal direction, until a second catch step 9 is reached in which the auxiliary medical material 3 is positioned inside the application tube 1 and cannot be wound down again off the winding insert 2 through the at least one gap 6 of the application tube 1.

In this working step the application tube 1 together with the inserted winding insert 2 is inserted into the surgical area, for instance by means of a trocar sleeve. In the surgical area the winding insert 2 is then inserted into the application tube 2 as far as the third catch step 9, in which the winding insert 2 wound up together with the auxiliary medical material 3 that is to be applied again emerges out of the application tube 1 on the distal end. Now the auxiliary medical material 3 can be grasped, for instance by a grip forceps. By rotating the winding insert 2 the auxiliary medical material 3 can now be easily and securely wound off of the winding insert 2 on the spot and applied to the surgical site that is to be treated.

A device of this design for intracorporeal application of auxiliary medical material 3 is distinguished in that it is of simple structure and ensures ease of operation as well as safe protective transport all the way to the surgical area of the auxiliary medical material 3 that is to be applied.

The invention claimed is:

1. A device for intracorporeal application of an auxiliary medical material, the device comprising:
    a hollow application tube for inserting the auxiliary medical material into a surgical area, the application tube having at least one window thereon, wherein the at least one window is spaced away from a distal opening of the application tube; and
    a winding insert configured to be inserted into the application tube, the winding insert having a distal portion onto which the auxiliary medical material is wound and a proximal portion that comprises a various catch steps, the various catch steps being spaced apart from each other in an axial direction of the winding insert such that each catch step marks a corresponding working step and a particular insertion depth of the winding insert inside the hollow application tube;
    wherein the application tube and the winding insert are configured such that:
        i) at a first catch step and a first corresponding working step, the auxiliary medical material can be inserted through the at least one window to wind onto the winding insert while the distal portion is completely inside the application tube;
        ii) at a second catch step and a second corresponding working step, the distal portion is inserted distally farther into the application tube than at the first catch step and the auxiliary medical material cannot be unwound through the at least one window; and
        iii) at a third catch step and a third corresponding working step, the distal portion and the auxiliary medical material extend through the distal opening of the application tube.

2. The device according to claim 1, wherein the application tube defines a longitudinal axis and wherein the winding insert, when inserted into the application tube, can be rotated within the application tube about the longitudinal axis.

3. The device according to claim 2, wherein the auxiliary medical material can be affixed onto the winding insert.

4. The device according to claim 1, wherein the auxiliary medical material can be affixed onto the winding insert.

5. The device according to claim 4, wherein a slit is configured in the winding insert for receiving one end of the auxiliary medical material.

6. The device according to claim 4, wherein a slit is configured to traverse entirely through the winding insert for receiving the auxiliary medical material.

7. The device according to claim 1, wherein the winding insert, at least in the distal portion, is configured as a wire pin that can be inserted into the application tube.

8. The device according to claim 1, wherein the at least one window extends in an axial direction on the application tube.

9. The device according to claim 8 wherein the at least one window comprises two axially-extending windows on diametrically opposite sides of the application tube.

10. The device according to claim 1, further comprising a handle positioned on the proximal end of the application tube and of the winding insert.

11. The device according to claim 1, wherein the auxiliary medical material consists of a mesh bio-material for a hernia operation.

12. The device according to claim 1, wherein the auxiliary medical material that is to be applied comprises bio-materials or wound applications.

13. The device according to claim 1, further comprising a handle positioned on the proximal end of the application tube or of the winding insert.

* * * * *